(12) United States Patent
Vestevich et al.

(10) Patent No.: US 8,394,428 B1
(45) Date of Patent: Mar. 12, 2013

(54) FORMULATIONS AND METHODS FOR PREVENTING EYEBROW HAIR LOSS

(75) Inventors: Renata Marie Vestevich, Bloomfield Hills, MI (US); Arun Nandagiri, Libertyville, IL (US)

(73) Assignee: RMV Trademarks, LLC, Bloomfield Hills, MI (US)

( * ) Notice: Subject to any disclaimer, the term of this patent is extended or adjusted under 35 U.S.C. 154(b) by 0 days.

(21) Appl. No.: 13/229,253

(22) Filed: Sep. 9, 2011

Related U.S. Application Data

(63) Continuation of application No. 12/950,330, filed on Nov. 19, 2010, now abandoned.

(60) Provisional application No. 61/353,926, filed on Jun. 11, 2010.

(51) Int. Cl.
*A61K 36/00* (2006.01)

(52) U.S. Cl. ........................................................ 424/725
(58) Field of Classification Search .................. None
See application file for complete search history.

(56) References Cited

U.S. PATENT DOCUMENTS 7,179,494 B1 * 2/2007 Marchese et al. ............. 424/725
2009/0291101 A1 * 11/2009 France ..................... 424/195.17

* cited by examiner

*Primary Examiner* — Qiuwen Mi
(74) *Attorney, Agent, or Firm* — McDonnell Boehnen Hulbert & Berghoff LLP

(57) ABSTRACT

Compositions comprising from about 0.5 to about 40 percent by weight of black cohosh extract, from about 0.5 to about 20 percent by weight of nonionic surfactant, and from about to 40 about 99 percent by weight of hydroxylated solvent are effective in reducing and preventing eyebrow hair loss in patients undergoing chemotherapy.

25 Claims, No Drawings

FORMULATIONS AND METHODS FOR PREVENTING EYEBROW HAIR LOSS

CROSS REFERENCE TO RELATED APPLICATIONS

This application is a continuation of U.S. application Ser. No. 12/950,330 (now abandoned), filed Nov. 19, 2010, which claims the benefit of U.S. Provisional Patent Application No. 61/353,926, filed Jun. 11, 2010, the entire contents of which are incorporated herein by reference.

BACKGROUND

Hair is composed of keratin, a tough and insoluble protein. Each individual hair comprises a cylindrical shaft and a root, and is contained in a follicle, a flask-like depression in the skin. The bottom of the follicle contains a finger-like projection termed the papilla, which consists of connective tissue from which hair grows, and through which blood vessels supply the cells with nourishment. The shaft is the part of the hair that extends outwards from the skin surface, and the root is the part of the hair that remains buried beneath the skin surface. The base of the root expands into a hair bulb, which rests upon the papilla. Cells from which the hair is produced grow in the bulb of the follicle and are extruded in the form of fibers as the cells proliferate in the follicle. "Hair growth" refers to the formation and elongation of the hair fiber by the dividing cells.

Hair growth occurs by a cycle of activity that is divided into three stages: anagen, catagen, and telogen. Anagen is the active phase, during which the epidermal stem cells of the dermal papilla divide rapidly. Daughter cells move upward and differentiate to form the concentric layers of the hair itself. Catagen is the transitional stage, where follicular stem cell division has ceased. Telogen is the resting stage, where the hair is retained for several weeks before an emerging new hair developing below it dislodges the telogen-phase shaft from its follicle. Hair is thus undergoing constant renewal. Among approximately 125,000-150,000 hairs on a scalp, at any given time approximately ten percent are at rest and will be replaced within a few months.

The location in which hair originates affects its characteristics. Eyebrow hair, for example, differs from scalp hair in several respects. For eyebrow hair, the growth cycle is very short, typically completing in approximately 4 months, whereas the scalp hair growth cycle requires 3 to 4 years to complete. This difference in growth cycle duration is the reason eyebrow hairs are much shorter than scalp hairs. Another distinction is that eyebrow hair emerges from the follicle at a very acute angle, which produces growth that is essentially parallel to the skin surface. By contrast, the angle between scalp hair and the skin can be 45 degrees or more. Eyebrow hairs also grow as single strands, whereas several hair strands typically arise from a single follicle on the scalp.

Disruption of the hair growth cycle causes alopecia (hair loss), a condition that affects millions of men and women. Alopecia encompasses any loss of hair, including not only from the scalp, but also from other areas such as the eyebrows. Certain chemotherapeutic agents can induce alopecia. Chemotherapy works by damaging the structure or metabolism of rapidly dividing cells. Unfortunately, chemotherapeutic agents do not selectively target only diseased or otherwise undesirable cells, such as the rapidly proliferating tissue of a cancerous tumor, and instead also attack normal cells that multiply rapidly in the body, including those in bone marrow, the lining of the mouth, stomach, and hair follicles.

Due to its long anagen phase, the scalp is a common location for chemotherapy-induced hair loss. Hairs of the beard, eyebrows, eyelashes, axillary regions, and pubic regions are also variably affected by chemotherapy. During anagen, cells in the bulb of the hair follicle exhibit the greatest activity in building up the hair shaft. Chemotherapeutic agents impair mitotic and metabolic processes in actively growing hair follicles and lead to a weakening of the partially keratinized, proximal portion of the hair shaft, resulting in a thinning of the hair shaft, which becomes fragile and susceptible to breakage with minimal influence (anagen effluvium). Evidence exists suggesting that telogen hair is also lost during chemotherapy (telogen effluvium). Braun-Falco, Dynamics of normal and pathological hair growth, ARCH. KLIN. EXP. DERMATOL. 227(1):419-52 (1966).

In human skin, alopecia can start at any time after initiation of chemotherapy, but hair loss typically occurs 2 to 4 weeks after treatment begins. Hubbard, Chemotherapy-induced alopecia, CLIN. ONCOL. 4:387-457 (1985); Hussein, Chemotherapy-induced alopecia: New developments, SOUTHERN MED. J. 86:489-496 (1993). The rate and pattern of hair shedding varies with the degree to which anagen effluvium and telogen effluvium occur. Accordingly, the hair may fall out very quickly in clumps or it may fall out gradually.

The extent of chemotherapy-induced hair loss depends on the drug being used, how long the drug is used, and whether other treatments (such as radiation) are concurrently employed. There are four major classes of chemotherapeutic agents that can induce alopecia, with the extent of induced hair loss differing across the classes: antimicrotubule agents (e.g. paclitaxel (trade name Taxol®)); topoisomerase inhibitors (e.g. doxorubicin); alkylators (e.g. cyclophosphamide); and antimetabolites (e.g. 5-fluorouracil plus leucovorin). Drugs with high potential for inducing alopecia include adriamycin, cyclophosphamide daunorubicin, docetaxel (trade name Taxotere®), epirubicin, etoposide, ifosphamide, irinotecan, paclitaxel, topotecan, vindesine, and vinorelbine. Taxol® typically induces complete hair loss, including scalp and eyebrows. Adriamycin causes complete hair loss on the scalp, and very often causes loss of eyebrows in patients. Chemotherapeutic agents such as methotrexate, cytoxan, carboplatin, and 5-fluorouracil can cause hair loss in some patients but not others. There are many similar examples of chemotherapeutic agents that can induce partial or complete hair loss in various locations throughout the body. The overall incidence of chemotherapy-induced hair loss is estimated to be 65 percent. Trueb, Chemotherapy-induced alopecia, SEMIN. CUTAN. MED. SURG. 28(1):11-14 (2009).

Chemotherapy-induced alopecia can be profoundly traumatic, and ranks among the most psychologically devastating side-effects of cancer treatment. Kiebert et al. Effect of perioperative chemotherapy on the quality of life of patients with early breast cancer, EUR. J. CANCER 26:1038-1042 (1990); Macquart-Moulin et al. Discordance between physicians' estimations and breast cancer patients' self-assessments of side-effects of chemotherapy: an issue for quality of care, BR. J. CANCER 76:1640-1645 (1997). Indeed, studies show that for many women, losing their hair is more emotionally distressing than losing a breast, because one can conceal loss of a breast but hair loss is so obvious and apparent. For men as well, hair loss during chemotherapy can negatively affect perceptions of masculinity, and loss of eyebrows in particular provides an unwelcome signal of having cancer. More than 80 percent of patients who receive chemotherapy consider hair loss to be the worst aspect of their treatment (Kiebert et al.; Macquart-Moulin et al.), and 8 percent of female cancer patients would even decline treatment for fear of that side-effect. McGarvey et al., Psychological sequelae and alopecia among women with cancer, CANCER PRACT. 9(6):283-289 (2001); Munstedt et al., Changes in self-concept and body image during alopecia induced cancer chemotherapy, SUPPORT CARE CANCER 5(2):139-143 (1997). Although cranial prostheses (wigs) sometimes can be used to conceal loss of scalp hair, it is far more difficult to conceal loss of other facial hair, such as eyebrows. Eyebrows are a critical facial feature that serve to frame the eyes (the single most important facial element) and they convey key non-verbal information.

Though the structure and growth cycle of hair is well known, the exact mechanism(s) by which chemotherapeutic agents cause hair loss is not well understood. Although morphological changes that occur in hair follicles during chemotherapy were initially described in the early 1960s, there has been little progress in elucidating the mechanism(s) underlying such morphological changes.

Several diverse measures have been suggested for limiting or preventing chemotherapy-induced alopecia. Some researchers suggest that massive induction of apoptosis (a process of programmed cell death (PCD) that may occur in multi-cellular organisms) in the hair follicle is one mechanism by which chemotherapeutic agents damage growing hair follicles. These researchers propose that a pretreatment with topical calcitriol-analogs can suppress chemotherapy-induced apoptosis in vivo. Schilli et al., Reduction of Intrafollicular Apoptosis in Chemotherapy-Induced Alopecia by Topical Calcitriol-Analogs, J. INVESTIGATIVE DERM. 111:598-604 (1998). However, topical application of 1,25-dihydroxyvitamin $D_3$ failed to prevent or retard hair loss in human scalp after administration of cyclophopshamide. Hidalgo et al., A phase I trial of topical topitriol (calcitriol, 1,25-dihydroxyvitamin $D_3$) to prevent chemotherapy-induced alopecia, ANTICANCER DRUGS 10:393-395 (1999).

Other investigators suggest that cleansing follicle openings of sebum may reduce hair loss and reduce the time necessary for hair re-growth in cancer patients who undergo chemotherapy. For example, U.S. Pat. No. 6,139,828 to McCullough discloses compositions for cleansing the scalp and hair follicles. However, the disclosed compositions include anionic surfactants, which can be harsh and irritating. Moreover, the disclosure provides only a single example of use of the claimed compositions in a patient undergoing chemotherapy. Though that example suggests that the patient experienced hair re-growth while continuing chemotherapy and radiation treatments, the disclosure provides no information regarding the patient's previous or current chemotherapy regimen. Because certain chemotherapeutic agents do not cause hair loss, it is not clear whether that patient experienced hair re-growth due to application of the disclosed composition, or instead simply due to natural hair re-growth where the presently-employed chemotherapeutic agent was one that did not induce hair loss. Furthermore, the disclosure nowhere discusses or exemplifies preventing (as opposed to reducing) hair loss in chemotherapy patients, and nowhere discusses or exemplifies reducing or preventing eyebrow loss.

Still other researchers suggest that scalp cooling may be effective in preventing hair loss in patients treated with certain chemotherapeutic agents. Such proponents contend that cooling the scalp to a temperature that produces a subcutaneous temperature of 20° C. (68° F.) constricts blood supply to hair follicles, preventing high chemotherapy dose delivery during the initial phase of treatment, and reducing metabolic rate of hair follicle cells. However, such treatment can be uncomfortable for a patient to endure. Moreover, scalp cooling does not prevent loss of other facial hair, such as eyebrows.

Still further methods that do not interact directly with existing hair follicles have also been proposed for concealing hair loss, and in particular eyebrow loss. For example, micropigmentation (tattooing) is sometimes used to simulate eyebrows that have been permanently lost. Micrograft transplants can also sometimes be used to restore eyebrows. However, such methods are time-consuming, often painful, and expensive.

As the discussion above demonstrates, previously proposed treatments for preventing chemotherapy-induced hair loss are uncertain and unsatisfactory in many respects. So far, no satisfactory composition or method exists for limiting or preventing chemotherapy-induced alopecia in humans. Accordingly, there remains a need for compositions and methods for preventing hair loss in patients undergoing chemotherapy, and in particular for preventing eyebrow loss in such patients.

SUMMARY

In one aspect, the present invention provides a composition comprising from about 0.5 to about 40 percent by weight of black cohosh extract, from about 0.5 to about 20 percent by weight of nonionic surfactant, and from about to 40 about 99 percent by weight of hydroxylated solvent.

In another aspect, the present invention provides a method for treating hair comprising use of a composition comprising from about 0.5 to about 40 percent by weight of black cohosh extract, from about 0.5 to about 20 percent by weight of nonionic surfactant, and from about to 40 about 99 percent by weight of hydroxylated solvent.

In yet another aspect, the invention provides a method for reducing or preventing loss of eyebrows in chemotherapy patients, comprising use of a composition comprising from about 0.5 to about 40 percent by weight of black cohosh extract, from about 0.5 to about 20 percent by weight of nonionic surfactant, and from about to 40 about 99 percent by weight of hydroxylated solvent.

Embodiments of the present invention may pertain to one or more of these aspects, or to other aspects disclosed herein. These and other aspects and advantages of the present invention will be apparent to those of ordinary skill in the art from the disclosure herein, and in particular from the following detailed description of the invention.

DETAILED DESCRIPTION

It has been surprisingly found that certain compositions containing black cohosh extract are effective in reducing and preventing hair loss, particularly the loss of eyebrows, in patients undergoing chemotherapy. Compositions of the present invention comprise from about 0.5 to about 40 percent by weight of black cohosh extract, from about 0.5 to about 20 percent by weight of nonionic surfactant, and from about to 40 about 99 percent by weight of hydroxylated solvent. The compositions disclosed herein may also optionally include one or more additives. Compositions of the invention may be in any form suitable for topical administration, including but not limited to liquids, gels, pastes, or emulsions.

Black Cohosh

As used herein, the term "black cohosh extract" refers to an extract from one or more portions of the black cohosh plant, or to a solution containing an equivalent amount of the active ingredient(s) thereof. As used herein, the term "extract" refers to a concentrate of water-soluble and/or alcohol-soluble plant components from the portion of the plant extracted.

Black cohosh has peripheral vasodilatory and anti-inflammatory effects. The roots and rhizomes (underground stems) of black cohosh were long used medicinally by Native Americans to treat a host of conditions, including gynecological disorders, kidney disorders, malaria, and rheumatism. "Cohosh" is the Algonquin word for "gnarly root." Historically, black cohosh has been used as an anti-inflammatory and sedative in treating female reproductive complaints such as painful menstrual cramping, delayed periods, mastitis, ovarian pain and other menopausal symptoms. In the present day, black cohosh is most commonly used as a remedy for rheumatoid and myalgic pain, to control symptoms of menopause, and as an alternative to hormone replacement therapy with patients for whom such therapy is either refused or contraindicated.

Black cohosh is a member of the botanical family Ranunculaceae (buttercup family), and is a perennial plant native to temperate regions of the Northern Hemisphere. The taxonomic genus of the plant species black cohosh is a matter of dispute. In the eighteenth century, the Swedish botanist Carl Linnaeus classified the species within the genus *Actaea*. This designation was revised in the nineteenth century by the English botanist Thomas Nuttall, who reclassified the species into the genus *Cimicifuga*. Recent data from morphological and gene phylogeny analyses suggest that black cohosh is more closely related to species of the genus *Actaea* than to other *Cimicifuga* species, prompting some botanists to revise the black cohosh genus classification to *Actaea racemosa* as originally proposed by Linnaeus. Scientific debate regarding the proper taxonomic designation for black cohosh continues to this day. Accordingly, black cohosh is known as both *Actaea racemosa* and *Cimicifuga racemosa*. Other common names include baneberry, black snakeroot, black bugbane, bugbane, bugwort, fairy candle, macrotys, rattleroot, rattletop, rattleweed, and squawroot. Insects avoid the black cohosh plant, which accounts for some of its common names.

The genus *Cimicifuga* includes eighteen species, one of which is native to Europe, six of which are native to North America, and the remainder of which are native to northeast Asia. The genera *Actaea* and *Cimicifuga* when combined include 25 to 30 species. Thus, the black cohosh genus contains numerous species, and any suitable black cohosh plant within the black cohosh genus can be used as the source of the black cohosh extract used in compositions of the present invention.

The mechanism of action of black cohosh extract remains unclear. The chief constituent of black cohosh root is an amorphous resinous substance known as Cimicifugin or Macrotin. Studies show that black cohosh extract contains several compounds that may contribute to its activity, including triterpene glycosides (acetin, cimicifugoside, 26-deoxyactein), isoflavones (formononetin), organic acids (caffeic acid, fukinolic acid, isoferulic acid, salicylic acid), aglycones, resins (cimicifugin), phenols, and antioxidants (hydroxytyrosol). The biological activity of black cohosh cannot as yet be attributed to any one chemical component or group of components.

Black cohosh extract used in compositions of the present invention can be obtained from one or more portions of the black cohosh plant. In the present invention, the black cohosh extract is preferably taken from the root and rhizome of the plant. The black cohosh plant can be prepared for extraction by subdividing the plant into small pieces. The small pieces are ground into a powder form, such as by mechanical disruption in a blender or other similar means. If less than the whole plant is being used, the desired portions are first isolated from the remaining portions of the plant and then subdivided into small pieces and ground into a powder form.

Black cohosh extract can be prepared using either conventional or supercritical extraction techniques. Suitable supercritical extraction methods are disclosed in U.S. Pat. Nos. 5,932,101 and 5,120,558, both of which are incorporated by reference herein. Suitable conventional extraction techniques are disclosed in U.S. Pat. Nos. 5,891,440, 5,874,084, and 5,908,628, all of which are incorporated by reference herein. A preferred method is extraction with a lower alkyl alcohol. A preferred lower alkyl alcohol is isopropanol. The resulting extract may be maintained as a liquid or converted using conventional means to another form, such as a dried powder for later reconstitution. In some instances, black cohosh extract may be supplied as an aqueous solution. In other instances, black cohosh extract may be supplied as a solution of water and an alcohol such as isopropanol. In still other instances, black cohosh extract may be supplied as a solution of water and a hydroxylated solvent such as propylene glycol. Extracts of black cohosh are typically standardized to 26-deoxyactein content, and commercial preparations of black cohosh usually contain 1 mg of total triterpenes (expressed as 26-deoxyactein) in each 20-mg dose of extract.

Compositions of the invention may contain from about 0.5 to about 40 percent by weight of black cohosh extract, and more particularly from about 2 to about 35 percent by weight of black cohosh extract. More preferably, compositions of the invention contain from about 4 to about 25 percent by weight black cohosh extract. A preferred black cohosh extract is a 20-percent solution of *Cimicifuga racemosa* root extract in a propylene glycol/water mixture, but others may be used as well.

Nonionic Surfactant

As used herein, the term "nonionic surfactant" refers to any surfactant lacking a charge in its hydrophilic portion. Also as used herein, the term "nonionic surfactant" refers to any suitable nonionic surfactant or mixture of two or more nonionic surfactants.

Nonionic surfactants are well known in the art, and the present invention may employ any nonionic surfactant or mixture thereof that is suitable for application to skin or hair and is compatible with other ingredients present in the composition. Suitable nonionic surfactants are described in McCutcheon's, Detergents and Emulsifiers, North American edition (1986), published by allured Publishing Corporation; McCutcheon's, Functional Materials, North American Edition (1992); International Cosmetic Ingredient Dictionary and Handbook, $7^{th}$ ed. (1997), published by the Cosmetic, Toiletry, and Fragrance Association; and U.S. Pat. No. 3,929,678 issued to Laughlin, et al on Dec. 30, 1975, all of which are incorporated by reference herein.

Most commonly, nonionic surfactants are compounds produced by the condensation of an alkylene oxide (hydrophilic in nature) with an organic hydrophobic compound which is usually aliphatic or alkyl aromatic in nature. The length of the hydrophilic or polyoxyalkylene moiety which is condensed with any particular hydrophobic compound can be readily adjusted to yield a water-soluble compound having the desired degree of balance between hydrophilic and hydrophobic elements. Another variety of nonionic surfactant is the semi-polar nonionic typified by the amine oxides, phosphine oxides, and sulfoxides.

Non-limiting examples of nonionic surfactants suitable for use in the present invention include fatty alcohols (including but not limited to cetyl alcohol, stearyl alcohol, cetostearyl alcohol, and oleyl alcohol); polyoxyethylene glycol alkly ethers (including but not limited to polyoxyethylene lauryl ether (Brij® 35)); polyoxypropylene glycol alkyl ethers; glucoside alkyl ethers; polyoxyethylene glycol octylpohenol ethers (including but not limited to Triton® X-100); polyoxyethylene glycol alkylphenol ethers (including but not limited to nonoxynol-9); glycerol alkyl esters; polyoxyethylene glycol sorbitan alkyl esters (including but not limited to polysorbate-20 and polysorbate-80); sorbitan alkyl esters (including but not limited to Span®-20 and Span®-80); block copolymers of polyethylene glycol and polypropylene glycol (including but not limited to poloxamer-407); amine oxides; and sulfoxides.

Preferred nonionic surfactants for use in compositions of the present invention are polyoxyethylene glycol sorbitan alkyl esters. Most preferably, the nonionic surfactant is a polyoxyethylene derivative of sorbitan monolaurate such as polysorbate 20. The compositions of the invention may contain from about 0.5 to about 20 percent by weight of a nonionic surfactant, and more particularly from about 1 to about 10 percent by weight of a nonionic surfactant. More preferably, compositions of the invention contain from about 4 to about 6 percent by weight of a nonionic surfactant.

Hydroxylated Solvent

Compositions of the present invention include one or more hydroxylated solvents. As used herein, the term "hydroxylated solvent" refers to any solvent or mixture of solvents containing at least one hydroxyl group. Suitable hydroxylated solvents include water, monohydric alcohols, polyhydric alcohols, or mixtures thereof. Water is a preferred hydroxylated solvent.

Monohydric alcohols that may be used in compositions of the present invention include but are not limited to $C_1$ to $C_6$ alcohols. Preferred monohydric alcohols include methanol, ethanol, n-propanol, isopropanol, n-butanol, isobutanol, t-butanol, and mixtures thereof. Isopropanol is a preferred monohydric alcohol.

Polyhydric alcohols that may be used in compositions of the present invention include but are not limited to glycols such as ethylene glycol, propylene glycol, glycerol, and polyol monoethers. Propylene glycol is a preferred polyhydric alcohol.

Preferably, the hydroxylated solvent comprises a mixture of water and a monohydric alcohol, or a mixture of water and a polyhydric alcohol. Most preferably, the hydroxylated solvent comprises a mixture of water, a monohydric alcohol, and a polyhydric alcohol.

Optional Components

The compositions of the invention may optionally contain additives, for example preservatives, colorants, agents to adjust pH, and fragrances. Any of the many preservatives well known in the art can be used. Preservatives for use with the invention particularly include but are not limited to phenoxyethanol/ethylhexylglycerin, methylparaben, and propylparaben. In certain cases, however, it may be desirable to minimize or eliminate use of paraben-based preservatives to improve consumer acceptance.

The pH of the compositions of the invention may be adjusted to maximize compatibility with skin and/or to increase or decrease the dermal and/or follicular penetration of the composition, as appropriate. In certain embodiments, the pH of the compositions of the invention is from about 4 to about 8. In other embodiments, it may be from about 5 to about 6, or from about 7 to about 8. Any of the many pH-adjusting ingredients well known in the art can be used. The pH-adjusting ingredients for use with the invention particularly include but are not limited to citric acid and triethanolamine.

The compositions of the present invention may be used to treat hair, and may be administered by any method known in the art. Preferably, the compositions are administered directly to the site where reducing or preventing hair loss is desired. In particular, the present invention includes methods for reducing or preventing loss of eyebrows in chemotherapy patients using a composition as disclosed herein.

All percentages used herein are by weight unless otherwise specified. Various embodiments and/or features are disclosed herein. As will be apparent to the ordinarily skilled practitioner, all combinations of such embodiments and features are possible and many such combinations can result in preferred executions of the invention.

The methods and compositions described herein as representative preferred embodiments are exemplary and are not intended as limitations on the scope of the invention. Modifications thereto will be evident to those skilled in the art, and are encompassed within the spirit of the invention. The terms and expressions which have been employed are used as terms of description and not of limitation, and there is no intention by the use of such terms and expressions to exclude any equivalents of the features shown and described or portions thereof. Thus, it should be understood that although the present invention has been specifically disclosed by embodiments and optional features, modifications and variations of the concepts herein disclosed are considered to be within the scope of this invention as defined by the description and the appended claims.

The present invention may be better understood in light of the following examples, which are intended for illustration purposes only, and should not be construed as limiting the scope of the invention in any way.

EXAMPLES

1. Formulations

Two formulations were prepared by traditional methods known in the art. The first (known as CELL 1) is as follows:

| CELL 1 - Eyebrow Treatment | | |
|---|---|---|
| Ingredient | Function | Wt % |
| Water | Diluent/Carrier | 54.6 |
| Isopropanol | Diluent/Carrier | 15.0 |
| Polysorbate 20 | Surfactant | 5.0 |
| Actyphyte of Black Cohosh, Supplied as 20% Solution (*Cimicifuga Racemosa* Root Extract in Propylene Glycol/Water) | Active Extract | 25.0 |
| Euxyl PE 9010 (Phenoxyethanol/Ethylhexylglycerin) | Preservative | 0.1 |
| Methylparaben | Preservative | 0.1 |
| Propylparaben | Preservative | 0.1 |
| Caramel Color, 1% Prepared from Concentrate | Colorant | 0.1 |
| Citric Acid | pH Adjuster | QS pH 5.0-6.0 |

The second formulation (known as CELL 2) is as follows:

| CELL 2 - Eyebrow Treatment | | |
|---|---|---|
| Ingredient | Function | Wt % |
| Water | Diluent/Carrier | 54.6 |
| Isopropanol | Diluent/Carrier | 15.0 |
| Polysorbate 20 | Surfactant | 5.0 |
| Actyphyte of Black Cohosh, Supplied as 20% Solution (*Cimicifuga Racemosa* Root Extract in Propylene Glycol/Water) | Active Extract | 25.0 |
| Euxyl PE 9010 (Phenoxyethanol/ Ethylhexylglycerin) | Preservative | 0.1 |
| Methylparaben | Preservative | 0.1 |
| Propylparaben | Preservative | 0.1 |
| Caramel Color, 1% Prepared from Concentrate | Colorant | 0.1 |
| Triethanolamine, 85% | pH Adjuster | QS pH 8.0 |

2. Administration of Formulations to Patients

Efficacy of formulations described herein was evaluated in 9 subjects undergoing chemotherapy. CELL 1 was used with 4 of the 9 subjects, and CELL 2 was used with the remaining 5 subjects. Each subject applied the formulation to each eyebrow twice daily (morning and evening), starting one week prior to the first chemotherapy treatment and continuing for two months after the chemotherapy treatment was completed. The formulation was applied to eyebrows only.

Prior to each application of the formulation, the subject cleaned and completely dried his or her eyebrows. Using a clean cotton swab, the subject then applied the formulation to both eyebrows. The formulation was stored at room temperature in a tightly closed bottle between usage periods.

At interim periods and at the conclusion of the chemotherapy treatment, hair loss and/or retention was evaluated to assess efficacy of the formulation.

Data for each subject is summarized in the following examples:

Example 1

Gender: Female
Medical Diagnosis: Breast cancer
Chemotherapy regimen: Cytoxan and q Taxotere® (every three weeks×4 cycles)
Formulation applied: CELL 2
Final assessment: Eyebrows fully retained, despite complete body hair loss everywhere else.

Example 2

Gender: Female
Medical Diagnosis: Breast cancer
Chemotherapy regimen: Cytoxan and Taxotere® (every three weeks×4 cycles)
Formulation applied: CELL 1
Final assessment: Eyebrows fully retained, despite complete body hair loss everywhere else.

Example 3

Gender: Female
Medical Diagnosis: Breast cancer
Chemotherapy regimen: Cytoxan and Taxotere® (every three weeks×4 cycles)
Formulation applied: CELL 1
Final assessment: Eyebrows fully retained, despite extensive body hair loss everywhere else.

Example 4

Gender: Female
Medical Diagnosis: Breast cancer
Chemotherapy regimen: Taxotere®, Cytoxan, and Adriamycin
Formulation applied: CELL 2
Final assessment: Eyebrows fully retained, despite complete body hair loss everywhere else.

Example 5

Gender: Female
Medical Diagnosis: Breast cancer
Chemotherapy regimen: Adriamycin and Cytoxan (every 2 weeks×4 cycles), followed by Taxol® (every 2 weeks×4 cycles)
Formulation applied: CELL 1
Final assessment: Eyebrows 50% retained, despite complete body hair loss everywhere else. Subject omitted a few applications of the formulation during the final evaluation period.

Example 6

Gender: Female
Medical Diagnosis Bladder cancer
Chemotherapy regimen: Taxol® (every 3 weeks×3 cycles), followed by Carboplatin (every 3 weeks×3 cycles) and Gemzar
Formulation applied: CELL 2
Final assessment: Eyebrows 50% retained, despite complete body hair loss everywhere else. Subject omitted a few applications of the formulation during the final evaluation period.

Example 7

Gender: Female
Medical Diagnosis: Breast cancer
Chemotherapy regimen: Taxol® (4 cycles)
Formulation applied: CELL 1
Final assessment: Eyebrows fully retained, despite complete body hair loss everywhere else.

Example 8

Gender: Female
Medical Diagnosis: Breast cancer
Chemotherapy regimen: Cytoxan and Taxotere® (every three weeks×6 cycles)
Formulation applied: CELL 2
Final assessment: Eyebrows fully retained, despite complete body hair loss everywhere else.

Example 9

Gender: Female
Medical Diagnosis: Breast cancer
Chemotherapy regimen: Cytoxan and Adriamycin (every three weeks×4 cycles)
Formulation applied: CELL 2
Final assessment: Eyebrows fully retained, despite complete body hair loss everywhere else.

As the above examples demonstrate, compositions and methods of the invention are effective in reducing and preventing hair loss, particularly the loss of eyebrows, in patients undergoing chemotherapy. All subjects underwent a chemotherapy regimen that normally is associated with complete body hair loss, yet all retained some or all of their eyebrows. Subjects who complied fully with the application protocol fully retained their eyebrows despite experiencing complete body hair loss everywhere else.

The invention claimed is:

1. A composition, comprising:
   (a) from about 2 to about 40 percent by weight of black cohosh extract;
   (b) from about 0.5 to about 20 percent by weight of nonionic surfactant; and
   (c) from about 40 to about 97.5 percent by weight of hydroxylated solvent.

2. The composition of claim 1, having a pH of from about 4 to about 8.

3. The composition of claim 2, having a pH of from about 5 to about 6.

4. The composition of claim 2, having a pH of from about 7 to about 8.

5. The composition of claim 1, wherein the nonionic surfactant comprises a polyoxyethylene derivative of sorbitan monolaurate.

6. The composition of claim 5, wherein the polyoxyethylene derivative of sorbitan monolaurate is polysorbate 20.

7. The composition of claim 1, wherein the nonionic surfactant comprises a mixture of at least two nonionic surfactants.

8. The composition of claim 7, wherein the nonionic surfactant comprises a mixture of polysorbate 20 and at least one other nonionic surfactant.

9. The composition of claim 1, wherein the hydroxylated solvent is water.

10. The composition of claim 1, wherein the hydroxylated solvent comprises a monohydric alcohol.

11. The composition of claim 10, wherein the monohydric alcohol comprises a $C_1$ to $C_6$ alcohol.

12. The composition of claim 11, wherein the monohydric alcohol is isopropanol.

13. The composition of claim 1, wherein the hydroxylated solvent comprises a polyhydric alcohol.

14. The composition of claim 13, wherein the polyhydric alcohol is selected from the group consisting of ethylene glycol, propylene glycol, glycerol, polyol monoethers, and mixtures of two or more thereof.

15. The composition of claim 13, wherein the polyhydric alcohol is propylene glycol.

16. The composition of claim 1, wherein the hydroxylated solvent comprises a mixture of water and a monohydric alcohol.

17. The composition of claim 1, wherein the hydroxylated solvent comprises a mixture of water and a polyhydric alcohol.

18. The composition of claim 1, wherein the hydroxylated solvent comprises a mixture of water, a monohydric alcohol, and a polyhydric alcohol.

19. The composition of claim 18, wherein the monohydric alcohol is isopropanol.

20. The composition of claim 18, wherein the polyhydric alcohol is propylene glycol.

21. A composition, comprising:
   (a) from about 15 to about 30 percent by weight of a 20-percent solution of black cohosh extract in hydroxylated solvent;
   (b) from about 1 to about 10 percent by weight polysorbate 20;
   (c) from about 10 to about 20 percent by weight isopropanol; and
   (d) from about 40 to about 75 percent by weight water.

22. The composition of claim 21, having a pH of from about 5 to about 6.

23. The composition of claim 21, having a pH of from about 7 to about 8.

24. A composition comprising:
   (a) from about 4 to about 40 percent by weight of black cohosh extract;
   (b) from about 0.5 to about 20 percent by weight of nonionic surfactant; and
   (c) from about 40 to about 95.5 percent by weight of hydroxylated solvent.

25. A composition comprising:
   (a) from about 5 to about 40 percent by weight of black cohosh extract;
   (b) from about 0.5 to about 20 percent by weight of nonionic surfactant; and
   (c) from about 40 to about 94.5 percent by weight of hydroxylated solvent.

* * * * *